United States Patent [19]
Desantis

[11] Patent Number: 6,111,142
[45] Date of Patent: Aug. 29, 2000

[54] PROCESS FOR THE PREPARATION OF AN AMINOALCOHOL

[75] Inventor: Nicola Desantis, Milan, Italy

[73] Assignee: Dibra S.p.A., Milan, Italy

[21] Appl. No.: 09/402,347

[22] PCT Filed: Apr. 1, 1998

[86] PCT No.: PCT/EP98/01874

§ 371 Date: Oct. 4, 1999

§ 102(e) Date: Oct. 4, 1999

[87] PCT Pub. No.: WO98/45247

PCT Pub. Date: Oct. 15, 1998

[30] Foreign Application Priority Data

Apr. 4, 1997 [IT] Italy .................................. MI97A0782

[51] Int. Cl.$^7$ ..................................................... C07C 209/00
[52] U.S. Cl. ............................................................. 564/497
[58] Field of Search ............................................... 564/497

[56] References Cited

FOREIGN PATENT DOCUMENTS 0 470 004 A1  2/1992  European Pat. Off. .

*Primary Examiner*—Samuel Barts
*Attorney, Agent, or Firm*—Nixon & Vanderhye

[57] ABSTRACT

A process for the preparation of 3-amino-1,2-propanediol, commonly known as isoserinol, having an organic impurities content lower than 0.1% and an inorganic impurities content lower than 0.05%.

34 Claims, No Drawings

PROCESS FOR THE PREPARATION OF AN AMINOALCOHOL

This application is a 371 of PCT/EP98/01874 filed Apr. 1, 1998.

3-Amino-1,2-propanediol of formula (I), commonly known as isoserinol, is widely used as building-block of non-ionic iodinated X-ray contrast agents, as well as in the synthesis of antiinflammatories, analgesics and cosmetics.

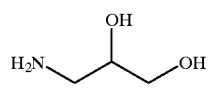
(I)

The major industrial application of said products lies in the synthesis of a number of non-ionic X-ray contrast agents, such as: Iohexol, Iopentol, Iopromide, Ioversol, Ioxilan, Iodixanol.

Physicians and the authorities which grant drug marketing authorizations, require drugs with very low levels of impurities in order to minimize any involved risks of side-effects or toxic effects for the patient.

As far as iodinated contrast agents are concerned, such a requirement is due to the total amount of administered product, which is much higher than that of other medicaments. By way of example, the injected dose of contrast agent can reach and even exceed 150 g.

The high purity level of the compound of formula (I) is therefore extremely important in order to avoid formation of any by-products and assure high purity standards to the final products.

In literature, a number of methods for the purification of compound (I) are reported, the most widely used being distillation under vacuum (see, for example, EP 470004), and other procedures to remove water contained in the crude, always under reduced pressure (JP 3063251) or to decolourize the solution, again under reduced pressure (JP 3086851).

Nevertheless, said product is marketed with impurity contents ranging from 1% to 3% (see for instance the product marketed by ALDRICH or by MERCK).

The major starting syntons for the synthesis being glycidol or 3-chloro-1,2-propanediol, which are reacted with ammonia (see, by way of example, the following patents: JP 03063251 A2; DE 3830351A1; DE 3014129A1; DE 3014109A1; DE 3014098A1), the main organic impurities which can be expected, and in some cases described, are: glycerin, serinol, 3-chloropropane-1,2-diol, bis(2,3-dihydroxypropyl)amine, tert(2,3-dihydroxypropyl)amine.

In addition to these impurities, some inorganic acids, such hydrochloric and sulfuric acids, and by-products such as 5-amino-2,4,6-triiodoisophthalic acid should also be considered in case compound of formula (I) derives from recovery of contrast agents.

Different purification procedures can be selected depending on the type of and the content in impurities present in 3-amino-1,2-propanediol.

Among organic impurities, serinol is very difficult to remove completely, since it has chemical characteristics similar to those of the compound of formula (I).

The present invention relates to novel processes for the purification of compound of formula (I), which can be applied directly on the product both as the free base and its salts, depending on the impurities present in the starting product.

Object of the present invention is a process for the purification of compound of formula (I) to obtain products with a content in organic impurities <0.1% and in inorganic impurities lower than 0.05%, comprising the following steps:

a) extraction of compound of formula (I) using either esters of acetic acid with ($C_1$–$C_5$) straight or branched alcohols or alcohol solvents of formula Alc—OH wherein Alc is a ($C_3$–$C_7$) straight or branched;

b) formation of the salts of compound of formula (I) with an acid selected from the group consisting of: oxalic acid, an X—Ph—COOH acid, wherein X is a substituent at the phenyl ring Ph such as H, Cl, $NO_2$, Br and ($C_1$–$C_4$) straight or branched alkyl, or p-toluenesulfonic acid;

c) crystallization of the salt formed in step b), using alcohol solvents of formula R—OH, wherein R is a ($C_1$–$C_6$) straight or branched alkyl, or monoalkylether glycols of the class of ($C_3$–$C_7$) alkylcellosolves, with water contents from 0.5% to 60%, depending on the used solvent;

d) release and purification from the salt by use of ion exchange resins, to give compound of formula (I) as the free base;

e) purification of the free base by crystallization using alcohols of formula R—OH.

The extraction with solvents at 20° C. to 50° C. provides a first rough removal of the organic impurities from the water-dissolved or melted product.

Said procedure can be carried out continuosly on the industrial scale, thereby performing effectively a first rough removal of the impurities extracted by the organic solvent. The organic impurities present can be appreciably removed using n-butyl acetate or n-pentanol.

About 20% of impurities can usually be removed, starting from very impure crude products from production cycles or from recovery cycles of the cited contrast agents.

In principle, the preparation of the salts of compound of formula (I) and the crystallization thereof is, for some salts, a procedure which provides highly pure products and which is selective, above all as far as glycerin, 3-chloropropane-1,2-diol and serinol are concerned.

The crystallization of the salts can be carried out in aqueous, hydro-organic or organic media.

In this case, the used solvents are alcohols of formula R—OH or monoalkylether glycols of the class of ($C_3$–$C_7$) alkylcellosolves. 2-Methoxyethanol, ethanol, n-butanol, 2-butanol, methanol are particularly preferred.

The compound of formula (I) is usually dissolved in water and reacted with the selected acid in aqueous medium at a temperature of 20° C. to 80° C.

After that, solvent is added to precipitate the salt by progressive cooling to a temperature of 20° C. to −5° C.

The water percentage can range from 0.5% to 60% (w/w), according to the salt and solvent used.

The salts of compound (I), whose purification has been investigated, are the following: hydrochloride, acid oxalate, benzoates of formula X—Ar—COOH, para-toluenesulfonate. More particularly, salts with ortho-chlorobenzoic acid, meta-nitrobenzoic acid and the acid salt with oxalic acid allow to remove completely the isomer 2-amino-1,3-propanediol.

It has also been found that step d), i.e. the preparation of the free base from said salts, yields to final products of the desired quality standards, removing completely the inorganic impurities, when carried out using ion exchange resins.

The use of cationic or anionic ion exchange resins, individually or in sequence, allows in fact to obtain the free base further purified by the chromatographic action effected by the resins themselves.

Such a technique is remarkably innovative compared with the chemical procedures making use of alkali or alkaline-earth bases to free said salts, in particular sodium hydroxide, potassium hydroxide and calcium hydroxide.

The crude salts resulting from step c) are then dissolved in water and freed on a cationic resin.

Preferred resins are C 20 MB (Duolite), IR 120 and Amberjet 1200 (Rhom & Haas) or, alternatively, the resin C 100 E (Purolite) or still C 350 MB (Dow).

Preferred anionic resins are Amberlite IRA 420 or Purolite A 400. In any case, similar cationic exchangers from different manufacturers can be used.

Isoserinol is then recovered from the cationic resin by elution with an ammonia aqueous solution.

In particular, the use of 4.7% aqueous ammonia as the base to elute isoserinol bound to the resin provides the complete elimination of inorganic impurities. The excess ammonia can be, in fact, easily removed by evaporation prior to the use of the crystallization techniques concerning the free base.

The use of said techniques, which have already been cited above as procedures for transforming the salts into the free bases without a significant loss of production, is advantageous on an industrial scale, for removing those organic by-products which cannot be salified by the resins themselves and, in general, for decolourizing the crude solutions.

A further advantage of said techniques is the easy automation of the process by means of a potentiometer, a conductimeter and a refractometer equipped with flow cells.

Said procedure, moreover, is greatly successful in case recovers of isoserinol from productive cycles of non-ionic X-ray contrast agents, such as Iohexol, Iomeprol, Iopentol and the like, are carried out.

The recovered crude product can in fact contain remarkable amounts of by-products from said procedures, such as triiodoaminoisophthaiic, triodohydroxyisophthalic acids or similar compounds, wherein the amino or phenol groups have been alkylated, amidated, esterified or etherified. In these cases, the use of the resins allows to easily remove iodinated by-products, recovering the purified compound of formula (I).

When an anionic resin is used, isoserinol is obtained directly in the eluate, whereas the acid is salified by the resin.

Such procedure makes use of the higher basicity of resin tertiary amines compared with isoserinol.

This procedure can be particularly advantageous when the free base is to be obtained from a crude solution containing a mixture of acids which salify isoserinol. The tree base or the hydrochloride, if the resin is regenerated in the Cl⁻ form, can thereby be obtained easily and directly.

The use of the resins in sequence (anionic and cationic) allows to free the base on the first column and to purify it from basic substances by chromatography on the second column, discarding heads and tails richer in by-products, such as the already cited tertiary and secondary amines.

The crystallization of the free base takes place when water content of the solvent ranges from 0.5% to 5%, depending on the solvent used. According to the procedure, a precipitation is carried out at temperatures ranging from −15° C. to 0° C., depending on the used solvent. Preferred solvents are n-butanol, 2-butanol, isobutanol and n-pentanol.

It should be stressed that the described techniques make it possible to remove organic by-products from the production cycle of X-ray contrast agents, and therefore this can be an important tool for also recovering serinol.

The present invention is highly innovative in that a high purity can be attained using the disclosed procedures, both in series and individually, using the crystallization of the free bases in organic solvents as the last step.

Particularly innovative are the methods for the crystallization of different salts of compound of formula (I) and the extraction techniques as well as the chromatographic purifications using ion exchange resins.

Said procedures are advantageous in that they are widely applicable on an industrial scale and they yield high quality products.

At present, all the marketed products, both as salts and as free bases of compound of formula (I), have a residual content in organic substances generally ranging from 0.4% to 2%. Moreover, the removal of the isomer down to levels lower than 0.1% is not always guarantied.

The procedures of the present invention provide pure products with a residual content in organic substances of 0.1%, with no appreciable residual inorganic substances, and they remove the isomer completely or anyhow to a content lower than 0.1%.

The analytical procedure used to evaluate the quality of the amino propanediols is that reported in literature by F. Uggeri et al., Journal of Chromatography, 432, 1988.

In order to further elucidate the object of the present invention, the salts which can be used for the compound (I), subdivided according to the type, are reported in the following, the operative procedures being illustrated in the examples.

1) Acid oxalate

Contrary to serinol, isoserinol can form the acid oxalate (Chem. Pharm. Bull., 122, 1983), which can be advantageously used in its purification, above all when removing its isomer and in general the other by-products.

This salt cannot be crystallized from water due to its high solubility, but it can easily be crystallized from organic or hydro-organic solutions, under the conditions described above.

The water amount for use in the crystallizations can range from 0% to 30% and the solvent to product ratio can range from 0.5:1 to 6:1 parts by weight.

2) Benzoates

The salts obtainable with benzoic acid and some derivatives, such as chlorobenzoates and nitrobenzoates, are particularly important due to their purifying activity.

Some procedures are particularly interesting as far as isoserinol in concerned, in that they allow to remove completely serinol, when present in a maximum starting content of 1.5%, particularly in the case of meta-nitrobenzoate and ortochloro-benzoate.

In principle, benzoates are capable of decreasing the content in organic by-products to levels lower than 0.1% in the compound of formula (I) recovered with the procedure above described for oxalate (use of resins and crystallization) and in yields >95%.

Isoserinol is easily salified by benzoic acid and by benzoates mono substituted at the ortho, meta or para positions with a halogen or a nitro group.

The solvents already cited above can be used.

The salt to solvent ratio can range from 1:0.5 to 1:5 parts by weight. The crystallization of the salt takes place from −5° C. to 0° C.

The free base is obtained from these salts also by means of ion exchange resins. Sulfonic resins regenerated in the sodium salt form are suitably used to promote the elimination of the water-soluble salified benzoate. After that, the free base is crystallized.

3) Para-toluensulfonates

Isoserinol is salified easily by paratoluenesulfonic acid. This salt also can be crystallized from the solvents mentioned above.

Also in this case, the obtainable yields are high, with an effective purification from most organic by-products, among which glycerin, which is completely removed.

The salt/solvent ratio can range from 1 to 5 parts by weight 0 and the crystallization temperature ranges from −5° C. to 0° C.

Yields above 85% can be obtained.

As a rule, it is possible to remove both some organic impurities with more lipophylic characteristics, making use of their higher solubility in solvents, and those substances having two amino groups, such as 2,3diaminopropanol, giving monobasic salts which are more soluble, particularly in low molecular alcohols.

The procedure using sulfonic cationic resins regenerated in the sodium form is not convenient to transform the salts into the free bases, although it can be employed.

On the other hand, the use of strong anionic resins regenerated in the form of either the free base or the chloride is more convenient for said salts, to bind paratoluenesulfonic acid on the resin and recovery the hydrochloride or the free base in solution.

Preferred resins are Amberlite IRA 420 (Rhom & Haas) and A 400 (Purolite).

Similar resins commercially available, manufactured by other producers, can also be used.

The obtained free base is then crystallized in good yields.

One or more of steps a); b); c); d) can be omitted when the crude product contains a slighter amount of impurities.

When the isomer serinol has to be removed completely, steps b) and c) are necessary, making use of the selectivity of some salts to these impurities.

In particular, crystallization of isoserinol acid oxalate from ethanol, orto-chlorobenzoate crystallized from isopropanol and meta-nitrobenzoate crystallized from ethanol containing 5% water (w/w), allow to remove the isomer serinol to below 0.05%.

Step a) involving the extraction has to be combined with other purification processes, in that it is a pre-treatment of compound of formula (I) when a high content in organic impurities is present.

Starting from impurity contents above 5%, each extraction can remove 5–10% of that impurity content. All the organic impurities from the syntheses of compound of formula (I) can be easily removed, and those impurities present in the recoveries of 3-amino-1,2-propanediol deriving from the processes for the preparation of iodinated contrast agents can be removed partially.

The preparation of the salts and the crystallization thereof are effective to decrease the level of organic impurities from 3%–5% to a lower value ranging from 0.5% to 1%, said process, if necessary, being repeated.

More specifically, glycerin is easily removed, as well as all those by-products which cannot give salts with the cited acids, whereas tertiary and secondary amines are partially removed in that their salts usually have a higher solubility in solvents than the salts of compound of formula (I).

Steps a), b), c) and d) can also be omitted in case the content in the isomer serinol is lower than 0.1% and the total organic impurities content is 0.3%, in this case being advisable to carry out the crystallization directly, provided no inorganic or ionic impurities from the production cycles of the X-ray contrast agents are present.

Crystallization from n-butanol, in particular, allows to remove partially the isomer serinol decreasing its content from 0.3% to 0.05–0.1%.

The use of ion exchange resins allows to remove all the inorganic impurities, even when starting from contents higher than 10%: in this case, the amount of the resin to use will be determined suitably.

The use of cationic resins provides the base freed from its salts without product losses and removes completely the ionic substances deriving from the production cycles of the contrast agents.

When secondary amines are present as by-products, see above cited impurities, the final fractions of the elution from the cationic resins will be suitably discarded, so that the impurity content will be decreased discarding the final fraction.

The following examples are intended to illustrate the best experimental conditions to carry out the process of this invention.

EXAMPLE 1

The starting product is crude isoserinol containing 10% of organic by-products, of which 0.7% is serinol and 8% is 5-amino-2,4,6-triiodo-1,3-benzenedicarboxylic acid.

456 g of oxalic acid dihydrate are suspended in 410 g of ethanol containing 6% water (by weight).

A solution is prepared separately dissolving 300 g of crude isoserinol in 300 g of ethanol containing 6% water (by weight), then the resulting solution is dropped in 30' into the suspension containing oxalic acid. After the addition, the mixture is cooled at 10° C. for 4 hours, then filtered washing with 150 g of 100% ethanol. The resulting product is dried under 12 mmHg at 60° C. for 12 hours, to give 570 g of acid oxalate.

Release of the base

The resulting product is dissolved in water to obtain a 15% by weight solution.

Said solution is percolated on 1300 ml of cationic resin AMBERJET 1200 regenerated in the acidic form, then the resin is washed until neutral pH. Isoserinol is then displaced from the resin with 1300 ml of 4.7% aqueous ammonia, eluting with approx. 2 BV/h.

The resin is washed to neutral pH with deionized water (approx. 2 liters). The resulting solution is concentrated to a residue, which is dissolved in 300 g of n-butanol, then cooled to −10° C., keeping said temperature for 6 hours.

Serinol is filtered, washed with 60 g of n-butanol cooled at 0° C. and dried at 30° C. under 3 mmHg vacuum for 12 hours.

Total yield 75%

Organic by-products 0.1%, of which isoserinol <0.05%.

EXAMPLE 2

2640 g of ethanol containing 5% water (by weight) are suspended in 550 g of m-nitrobenzoic acid, heating to 55° C., then 300 g of isoserinol containing 3% of organic by-products, of which 1% is serinol, are added, thereby increasing temperature of about 10° C. and causing a complete dissolution.

The salt is precipitated by cooling to 15° C. for 3 hours, then it is filtered and washed with 200 g of ethanol containing 5% water (by weight).

The product is dried at 50° C. under 14 mmHg for 12 hours, thereby obtaining 790 g of the salt. Yield: 92.9%.

Release of the base

The resulting product is dissolved in 1500 g of water to obtain a 15% by weight solution.

Said solution is percolated on 1300 ml of cationic resin AMBERJET 1200 regenerated in the sodium form, washing then the resin to obtain an eluate with specific conductivity <30 $\mu$S/cm.

Isoserinol is then displaced from the resin with 1300 ml of 4.7% aqueous ammonia, eluting with approx. 2 BV/h.

The resin is washed to neutral pH with deionized water (approx. 2 liters). The resulting solution is concentrated to a residue, which is dissolved in 300 g of n-pentanol, then cooled at −8° C., keeping said temperature for 6 hours.

Isoserinol is filtered, washed with 70 g of n-pentanol cooled at 0° C. and dried at 30° C. under 3 mmHg vacuum for 12 hours.

Total yield 87%

Organic by-products 0.1%, of which serinol <0.05%.

EXAMPLE 3

515.5 g of o-chlorobenzoic acid are dissolved in 2000 g of isopropanol heating to 50° C.

300 g of isoserinol containing 3% of organic by-products, of which 1.5% is serinol, are dissolved separately in 660 g of isopropanol.

The isoserinol solution is added drop by drop to the acid one at 50° in about 60', then cooled to 0–5° C., keeping this temperature for about 2 hours.

The resulting salt is filtered, washed with 400 g of isopropanol cooled at 0° C. and dried at 50° C. under 14 mmHg, to obtain 792 g of salt.

Yield 96.8%

Release of the base

The resulting product is dissolved in 1500 g of water to obtain a 15% by weight solution.

Said solution is percolated on 1300 ml of cationic resin AMBERJET 1200 regenerated in the sodium form, then the resin is washed to obtain an eluate with specific conductivity <30 μS/cm.

Isoserinol is then displaced from the resin with 1300 ml of 4.7% aqueous ammonia, eluting with approx. 2 BV/h.

The resin is washed to neutral pH with deionized water (approx. 2 liters). The resulting solution is concentrated to a residue, which is dissolved in 400 g of iso-butanol, cooled at −10° C. and kept at said temperature for 6 hours.

Isoserinol is filtered, washed with 10 g of iso-butanol cooled at 0° C., dried at 30° C. under 3 mmHg vacuum for 12 hours.

Total yield 93.5%

Organic by-products 0.1%, no serinol, ashes-free.

EXAMPLE 4

300 g isoserinol containing 1% of organic by-products are dissolved at 25° C. in 300 g of n-butanol.

The solution is cooled at −5° C., keeping said temperature for 12 hours. The residue is filtered and washed with 240 g of n-butanol cooled at 0° C.

Yield 95%

Content in total organic by-products 0.1%, ashes-free.

EXAMPLE 5

300 g of isoserinol containing 1.5% of organic by-products, of which 0.7% of serinol, are heated to 50° C. to obtain a melted product, which is then placed into a separatory funnel and washed three times with 900 g of butyl acetate.

The resulting product is dissolved at 50° C. in water to obtain a crude solution which is eluted on 1300 ml of cationic resin AMBERJET 1200 regenerated in the acidic form, washing with water to a specific conductivity <30 μS/cm.

Isoserinol is then displaced with 1400 ml of 5% aqueous ammonia eluting with approx. 2 BV/h, washing subsequently with water to neutral pH.

The eluate is concentrated under vacuum at a temperature of 50° C. in a rotary evaporator, to obtain a residue which cannot be distilled, which is taken up twice in 250 g of 2-butanol and evaporated to dryness.

The residue is dissolved in 200 g of 2-butanol, the resulting solution is cooled at −3° C., keeping said temperature for 4 hours and germinating.

The resulting solid is filtered and washed with 30 g of precooled solvent. The product is dried at 30° C. for 12 hours under 12 mmHg.

Yield 56%

Content in total organic by-products 0.1%, of which serinol 0.1%, ashes-free.

EXAMPLE 6

300 g of isoserinol containing 3% of organic by-products, of which 1.5% is serinol, are dissolved in 600 g of water, heating to 60° C., then 626.5 g of p-toluenesulfonic acid monohydrate are added in portions.

The solution is concentrated under vacuum at 50° C. to obtain a melted product with a water content from 20% to 40%. 600 g of absolute ethanol are added and the solution is refluxed.

The solution is distilled azeotropiclly, adding fresh dry solvent to an about 8% residual water content.

The solution is cooled slowly at 20° C., keeping said temperature for 3 hours. The salt is filtered and washed with 100 g of dry ethanol.

The resulting salt (about 700 g) is dissolved in water to obtain an approx. 10% solution.

Said solution is eluted on 5000 ml of anionic resin Amberlite IRA 420 and washed with water to neutral pH.

The resulting aqueous solution is concentrated to a residue and crystallized according to the procedure described in Example 5.

Yield 68%

Organic by-products <0.1%, ashes-free.

What is claimed is:

1. A process for the purification of isoserinol to obtain products with a content in organic impurities <0.1% and in inorganic impurities lower than 0.05%, comprising the following steps:

a) extraction of isoserinol using either esters of acetic acid with ($C_1$–$C_5$) straight or branched alcohols or alcohol solvents of formula Alc—OH wherein Alc is a ($C_3$–$C_7$) straight or branched chain;

b) formation of the salts of isoserinol with an acid selected from the group consisting of: oxalic acid, an X—Ph—COOH acid, wherein X is a substituent at the phenyl ring Ph such as H, Cl, $NO_2$, Br and ($C_1$–$C_4$) straight or branched alkyl, or p-toluenesulfonic acid;

c) crystallization of the salt formed in step b), using alcohol solvents of formula R—OH, wherein R is a ($C_1$–$C_6$) straight or branched alkyl, or monoalkylether glycols of the class of ($C_3$–$C_7$) alkylcellosolves, with water contents from 0.5% to 60%, depending on the used solvent;

d) release and purification from the salt by use of ion exchange resins, to give compound of formula (I) as the free base;

e) purification of the free base by crystallization using alcohols of formula R—OH.

2. A process according to claim 1, in which the solvent used in step a) is selected from butyl n-acetate and n-pentanol.

3. A process according to claim 1, in which the crystallization solvent in step c) is selected from the group consisting of: methanol, ethanol, n-butanol, 2-butanol, 2-methoxyethanol.

4. A process according to claim 1, in which the isoserinol salts are formed with the following acids: ortho-chlorobenzoic acid, meta-nitrobenzoic acid, oxalic acid, para-toluenesulfonic acid.

5. A process according to claim 4, in which serinol is removed completely below 0.05% by formation of the salts with ortho-chlorobenzoic acid, meta-nitrobenzoic acid or oxalic acid.

6. A process according to claim 5, in which the crystallization of isoserinol acid oxalate is carried out in ethanol.

7. A process according to claim 5, in which the crystallization of ortho-chlorobenzoate is carried out in isopropanol.

8. A process according to claim 5, in which the crystallization of meta-nitrobenzoate is carried out in ethanol containing 5% water (w/w).

9. A process according to claim 1, in which the free base is obtained from these salts by use of cationic resins regenerated in the sodium or acidic form.

10. A process according to claim 6, in which the resins are selected from the group consisting of: C 20 MB, Amberlite(R) IR 120, Amberjet(R) 1200, C 100 E, C 350 MB.

11. A process according to claim 6, in which isoserinol is recovered by displacement from the resin with aqueous ammonia.

12. A process according to claim 6, in which the progress of the elution of isoserinol from the resin is monitored by observation of pH and fractionation so as to discard those fractions richer in impurities.

13. A process according to claim 1, in which the free base is obtained from these salts by use of strong anionic resins.

14. A process according to claim 10, in which the resins are selected from the group consisting of: Amberlite(R) IRA 420, A 400 Purolite, SA 12 A, SBR-P.

15. A process according to claim 1, in which anionic and cationic resins are used in sequence.

16. A process according to claim 1, in which the crystallization of the free base is carried out when water content ranges from 0.5% to 5%, in precipitation phase, at a temperature from −15° C. to 0° C., depending on the solvent used.

17. A process according to claim 13, in which the crystallization of the free base is carried out in a solvent selected from the group consisting of: n-butanol, 2-butanol, isobutanol and n-pentanol.

18. A process for the preparation of isoserinol, with a serinol content lower than 0.05% and inorganic impurities content lower than 0.05%, in case the organic impurities content in the starting product does not exceed 0.3% and the content in the isomer serinol is lower than 0.15%, which process comprises the purification of the free base by crystallization using alcohols of formula R—OH, in which R—OH has the same meanings as in claim 1.

19. A process for the purification of isoserinol, comprising the following steps:
a) extraction of isoserinol using either esters of acetic acid with ($C_1$–$C_5$) straight or branched alcohols or ($C_3$–$C_7$) straight or branched alcohol solvents;
b) formation of a salt of isoserinol with an acid selected from the group consisting of: oxalic acid, an acid of formula X—Ph—COOH, wherein X is a substituent at the phenyl ring Ph such as hydrogen, Cl, $NO_2$, Br and ($C_1$–$C_4$) straight or branched alkyl, or p-toluenesulfonic acid;
c) crystallization of the salt obtained in step b) from a solvent selected from an R—OH alcohol, wherein R is a ($C_1$–$C_6$) straight or branched alkyl, or a monoalkylether glycol of the class of ($C_3$–$C_7$) alkylcellosolves, said solvent having a water content from 0.5 to 60%;
d) release and purification from the salt by elution through ion exchange resins to give isoserinol as the free base;
e) purification of the free base by crystallization from an alcohol as defined in step c).

20. A process according to claim 19, wherein the extraction temperature in step a) ranges from 20 to 50° C.

21. A process according to claim 19, wherein the crystallization solvent of step c) is selected from 2-methoxyethanol, ethanol, n-butanol, 2-butanol and methanol.

22. A process according to claim 19, wherein the salt from step c) is selected from oxalate, o-chlorobenzoate and m-nitrobenzoate.

23. A process according to claim 22, wherein the salt is acid oxalate, the water content ranges from 0 to 30% and the solvent to product ratio ranges from 0.5:1 to 6:1 parts by weight.

24. A process according to claim 22, wherein the salt is selected from chlorobenzoate and nitrobenzoate, the water content ranges from 0 to 30%, the solvent to product ratio ranges from 1:0.5 to 1:5 parts by weight and the base is released by elution through regenerated sulfonic resins.

25. A process according to claim 22, wherein the salt is para-toluenesolfonate, the water content ranges from 0 to 30%, the solvent to product ratio ranges from 1 to 5 parts by weight and the base is released by elution through strong anionic resins regenerated in the free base or the chloride forms.

26. A process according to claim 19, wherein the resin used in step d) is selected from DUOLITE C20 MB, IR 120, AMBERJET 1200, PUROLITE C100 e, PUROLITE A400, AMBERLITE IRA 420, PUROLITE A400.

27. A process according to claim 19, wherein isoserinol is displaced from the resin by means of aqueous ammonia.

28. A process according to claim 27, wherein 4.7% aqueous ammonia is used.

29. A process according to claim 19 and, wherein the anionic and cationic resins are in sequence.

30. A process according to claim 19, wherein the crystallization alcohol of step e) has a water content from 0.5 to 5%.

31. A process according to claim 19 wherein the crystallization alcohol is selected from n-butanol, 2-butanol, isobutanol and n-pentanol.

32. A process for the purification of isoserinol, comprising the crystallization of the free base from an R—OH alcohol, wherein R is a ($C_1$–$C_6$) straight or branched alkyl, said alcohol having a water content from 0.5 to 5%.

33. A process for the purification of isoserinol, in particular from its isomer serinol, comprising the following steps:
a) formation of a salt of isoserinol with an acid selected from the group consisting of: oxalic acid, an acid of formula X—Ph—COOH, wherein X is a substituent at the phenyl ring Ph such as H, Cl, $NO_2$, Br and a ($C_1$–$C_4$) straight or branched alkyl, or p-toluenesulfonic acid;
b) crystallization of the salt formed in step b) from a solvent selected from the group consisting of an R—OH alcohol, wherein R is a ($C_1$–$C_6$) straight or branched alkyl, or monoalkylether glycols of the class of ($C_3$–$C_7$) alkylcellosolves, with water contents from 0.5% to 60%;

c) release and purification from the salt by use of ion exchange resins, to give isoserinol as the free base;

d) purification of the free base by crystallization using alcohols of formula R—OH.

34. A process according to claim 33, wherein the crystallization solvent of step b) is n-butanol.

* * * * *